United States Patent
Bartee et al.

(10) Patent No.: US 8,721,735 B2
(45) Date of Patent: May 13, 2014

(54) PTFE COMPOSITE MULTI-LAYER MATERIAL

(76) Inventors: Chad M. Bartee, Lubbock, TX (US); Barry K. Bartee, Lubbock, TX (US)

( * ) Notice: Subject to any disclaimer, the term of this patent is extended or adjusted under 35 U.S.C. 154(b) by 272 days.

(21) Appl. No.: 12/876,737

(22) Filed: Sep. 7, 2010

(65) Prior Publication Data

US 2011/0060420 A1 Mar. 10, 2011

Related U.S. Application Data

(63) Continuation of application No. 11/354,272, filed on Feb. 14, 2006, now Pat. No. 7,789,888.

(60) Provisional application No. 60/653,069, filed on Feb. 14, 2005.

(51) Int. Cl.
*A61F 2/02* (2006.01)

(52) U.S. Cl.
USPC .................................................. 623/23.72

(58) Field of Classification Search
USPC ........... 623/1.42–1.48, 23.72–23.76; 422/221
See application file for complete search history.

(56) References Cited

U.S. PATENT DOCUMENTS

| | | | |
|---|---|---|---|
| 4,187,390 A | 2/1980 | Gore | |
| 4,531,916 A | 7/1985 | Scantlebury et al. | |
| 4,647,416 A | 3/1987 | Seiler et al. | |
| 4,743,480 A * | 5/1988 | Campbell et al. | 428/36.5 |
| 4,819,478 A | 4/1989 | Melcher | |
| 4,849,285 A | 7/1989 | Dillon | |
| 4,859,383 A | 8/1989 | Dillon | |
| 4,972,846 A | 11/1990 | Owens et al. | |
| 5,032,445 A | 7/1991 | Scantlebury et al. | |
| 5,093,179 A | 3/1992 | Scantlebury et al. | |
| 5,118,524 A | 6/1992 | Thompson et al. | |
| 5,171,148 A | 12/1992 | Wasserman et al. | |
| 5,196,016 A | 3/1993 | Buser et al. | |
| 5,197,882 A | 3/1993 | Jernberg | |
| 5,264,214 A | 11/1993 | Rhee et al. | |
| 5,356,429 A | 10/1994 | Seare | |
| 5,360,341 A | 11/1994 | Abramowitz | |
| 5,378,152 A | 1/1995 | Elia | |
| 5,380,328 A | 1/1995 | Morgan | |
| 5,443,483 A | 8/1995 | Kirsch | |
| 5,480,711 A * | 1/1996 | Ruefer | 428/315.5 |
| 5,511,565 A | 4/1996 | Syers | |
| 5,529,820 A | 6/1996 | Nomi et al. | |
| 5,545,226 A | 8/1996 | Wingo et al. | |
| 5,607,689 A | 3/1997 | Checchi | |
| 5,620,763 A | 4/1997 | House et al. | |
| 5,798,117 A | 8/1998 | New et al. | |
| 5,824,050 A | 10/1998 | Karwoski et al. | |
| 5,897,587 A | 4/1999 | Martakos et al. | |

(Continued)

*Primary Examiner* — Suzette J Gherbi
(74) *Attorney, Agent, or Firm* — Pillsbury Winthrop Shaw Pittman LLP

(57) ABSTRACT

A composite multi-layer material may generally comprise a d-PTFE material combined with an open structured material (either resorbable or non-resorbable) creating a composite multi-layer material. Attachment of the layers may be accomplished by stitching layers of material, exertion of hydraulic or other pressure, application of a biocompatible adhesive or heat, or some combination of the foregoing. Use of a d-PTFE, unexpanded material has multiple alternative uses, including without limitation, placement on the visceral side of a hernia that may minimize or even eliminate the incidence of abdominal adhesions. Alternatively, the material may be used to create tubing sufficient as a graft for treating abdominal aortic aneurysms.

27 Claims, 2 Drawing Sheets

(56) References Cited

U.S. PATENT DOCUMENTS

| | | | |
|---|---|---|---|
| 5,957,690 A | 9/1999 | Bartee et al. | |
| 5,993,972 A | 11/1999 | Reich et al. | |
| 6,019,764 A | 2/2000 | Bartee | |
| 6,022,553 A | 2/2000 | Anders et al. | |
| 6,025,044 A * | 2/2000 | Campbell et al. | 428/36.91 |
| 6,027,779 A * | 2/2000 | Campbell et al. | 428/36.91 |
| 6,075,180 A * | 6/2000 | Sharber et al. | 623/11.11 |
| 6,143,675 A * | 11/2000 | McCollam et al. | 442/221 |
| 6,299,637 B1 | 10/2001 | Shaolian et al. | |
| 6,306,424 B1 | 10/2001 | Vyakarnam et al. | |
| 6,325,627 B1 | 12/2001 | Ashman | |
| 6,409,764 B1 | 6/2002 | White et al. | |
| 6,547,820 B1 | 4/2003 | Staudenmeier | |
| 6,689,162 B1 | 2/2004 | Thompson | |
| 6,712,919 B2 | 3/2004 | Ruefer et al. | |
| 6,770,086 B1 * | 8/2004 | Girton | 623/1.13 |
| 7,296,998 B2 * | 11/2007 | Bartee et al. | 433/215 |
| 7,462,675 B2 | 12/2008 | Chang et al. | |
| 7,557,167 B2 | 7/2009 | Swetlin et al. | |
| 7,789,888 B2 * | 9/2010 | Bartee et al. | 606/151 |
| 2002/0031628 A1 * | 3/2002 | Zumbrum et al. | 428/36.9 |
| 2002/0111667 A1 | 8/2002 | Girton et al. | |
| 2005/0102036 A1 * | 5/2005 | Bartee et al. | 623/23.76 |
| 2005/0165447 A1 * | 7/2005 | Crawley et al. | 606/228 |
| 2005/0288767 A1 * | 12/2005 | Kujawski et al. | 623/1.13 |
| 2006/0253203 A1 * | 11/2006 | Alvarado | 623/23.74 |
| 2006/0280767 A1 * | 12/2006 | Hayashi | 424/423 |
| 2006/0282103 A1 * | 12/2006 | Fricke et al. | 606/151 |
| 2008/0133010 A1 * | 6/2008 | Bartee et al. | 623/16.11 |
| 2009/0216338 A1 | 8/2009 | Gingras et al. | |

* cited by examiner

PTFE COMPOSITE MULTI-LAYER MATERIAL

CROSS-REFERENCE TO RELATED APPLICATION

The present application is a continuation of U.S. patent application Ser. No. 11/354,272, filed Feb. 14, 2006 (U.S. Pat. No. 7,789,888), which claimed the benefit of U.S. Provisional Application Ser. No. 60/653,069, filed Feb. 14, 2004, entitled "COMPOSITE PTFE RECONSTRUCTIVE MESH," and both applications are incorporated herein by reference for all purposes. The present application is related to U.S. Pat. No. 5,957,690, issued Sep. 28, 1999, which is incorporated herein by reference and U.S. patent application Ser. No. 10/947,066, filed Sep. 21, 2004, which is incorporated herein by reference.

FIELD OF THE INVENTION

Aspects of the present invention relate generally to implantable medical products and more particularly to a high density unexpanded, unsintered polytetrafluoroethylene (d-PTFE) for use in tissue repair, reconstruction, grafting and regeneration.

BACKGROUND

Traditional repair, reconstruction and grafting of soft tissue and vascular tissue require techniques utilizing a reconstructive material or vascular prostheses. For instance, in hernia repair, currently marketed mesh devices generally include a laminated expanded polytetrafluoroethylene (e-PTFE) structure, using e-PTFE laminated to one or more sheets of e-PTFE or to a polypropylene mesh. The rationale for using e-PTFE is to minimize post-operative abdominal adhesions to the mesh. The currently marketed products use e-PTFE on the visceral side (bowel side) and an open pore material such as polypropylene mesh on the fascia or muscular side. The open structured polypropylene material is believed to promote tissue in-growth into the material, thus creating a strong reconstruction.

Postoperative adhesions continue to present significant clinical problems, however, and result in morbidity, mortality, and increased cost. With over 700,000 hernia operations per year, the frequency of secondary procedures to eliminate or otherwise to treat abdominal adhesions is generally in a range of about 50-60%, sometimes higher. No cause for these adhesions is known. While products employing e-PTFE attempt to minimize the incidence of adhesions as a result of the limited porosity and biocompatible nature of the material, the continued high level of adhesion incidence is representative of a clear deficiency in currently marketed technology.

Currently, surgery is the primary option for hernia repair and there are two primary methods of repair: tension repair and tension-free repair. For many years, tension repair was the only method for treating hernias. Tension repair involves incising the abdomen, pushing the protruding tissue back into the abdominal cavity and stitching the incision. It should be noted that while effective, this method causes severe patient discomfort and requires substantial recovery time relative to more modern repair methods.

Tension-free surgery is more commonly used in hernia repair today. It requires less time for recovery vis-à-vis the tension repair method. The tension-free repair method involves incising the abdomen, pushing the protruding tissue back into place and placing a piece of mesh either over or under the defect, which is then sutured into place. The mesh prevents the tissue from protruding through the hole.

Some hernia repair devices use porcine small intestinal submucosa to provide a scaffold for host cells to replace and repair damaged tissue. Once implanted into the hernia defect, host tissue cells and blood vessels colonize the graft and allow for site-specific tissue remodeling. The porcine small intestine tissue is gradually replaced by host tissue. However, the use of animal tissue poses both host immune response tissue rejection problems and potential for transmitted disease from animal to human.

Many types of mesh currently on the market are subject to shrinkage or migration. As a result, use of these products can lead to pain and bowel complications, which in turn may lead to infection.

Vascular repair and requires the use of graft tubing. For instance, abdominal aortic aneurysm repair traditionally requires a large incision in the abdominal wall from just below the sternum to the top of the pubic bone. After the intestines and internal organs of the abdomen are pulled aside, the aorta is clamped and the aneurysm cut open. After removing any damaged tissue, an aortic graft is sewn into the healthy aortic tissue both above and below the weakened area to create a bridge for proper blood flow. Typically, after the graft has been sewn into place, the tissue remaining from the aneurysm sac is loosely sewn over the new graft to prevent the new graft from rubbing against the intestine.

An alternative abdominal aortic aneurysm repair procedure uses an x-ray imaging device to deliver catheter (tube) containing a graft. The catheter is inserted into a blood vessel in the groin and guided to the aorta. Once in the aorta, a balloon at the catheter's tip is inflated and the graft tubing is expanded to a diameter necessary to preclude blood from flowing into the aneurysm. The catheter is removed by deflating the balloon and withdrawing it from the leg. The graft permits the flow of blood through the aorta to the arteries in the pelvis and lower extremities while bypassing the aneurysm.

SUMMARY

In accordance with some embodiments of a composite multi-layer material, d-PTFE may be combined with an open structured material (either resorbable or non-resorbable) creating a composite multi-layer structure. It will be appreciated that such attachment may be accomplished by stitching layers of material, exertion of hydraulic or other pressure, application of a biocompatible adhesive or heat, or some combination of the foregoing. One or more combinations may be used in the laminating process. A composite multi-layer material constructed and operative in accordance with the present disclosure may have utility in applications related to the reconstruction of soft tissue defects of the chest and abdomen.

Because d-PTFE has no substantially defined internodal distance and can be manufactured with significantly less porosity than e-PTFE, and because it has exhibited no tendency to form adhesions when used in oral and maxillofacial surgical applications, the use of a d-PTFE, unexpanded material on the visceral side of a soft tissue composite multi-layer material may minimize or even eliminate the incidence of abdominal adhesions and post-operative complications as compared to existing devices. In addition, it will be appreciated that the material may be used to create a tube for use as a vascular prosthetic capable of permitting blood flow through the interior of the graft while providing an open structured material on the exterior to permit tissue colonization.

The term sintered is a term well known in the art and is used herein consistent with that understanding. The term unsintered is used herein to describe PTFE polymer that has not been subjected to the sintering process. Unsintered PTFE is substantially unexpanded and contains no substantially defined internodal distance, which substantially reduces its porosity relative to e-PTFE. The limited porosity of the unsintered, substantially unexpanded PTFE substantially reduces tissue adhesions to the d-PTFE or migration of tissue into the d-PTFE. However, the limited porosity allows for the passage of ions and other small molecules necessary for cellular nourishment and waste transport.

BRIEF DESCRIPTION OF THE DRAWING FIGURES

DETAILED DESCRIPTION

Figure 2:
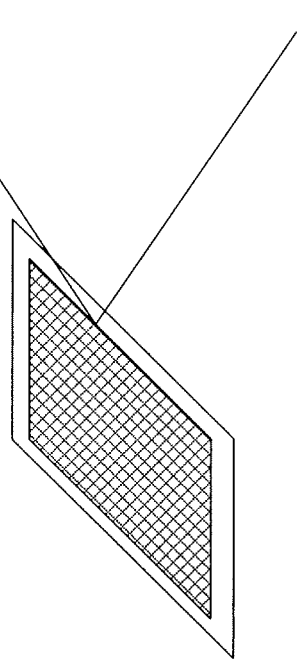
FIG. 2 is an exploded partial perspective diagram illustrating one embodiment of a composite multi-layer material.
Figure 1:
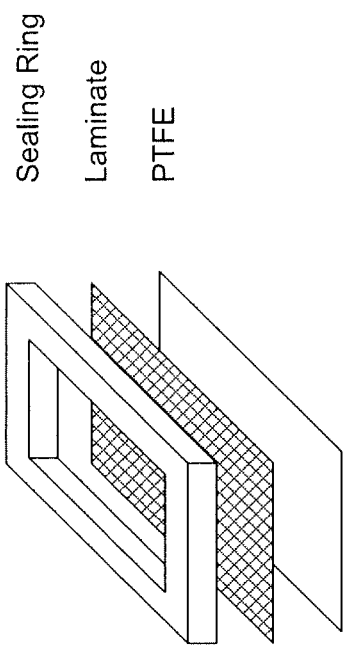
FIG. 1 is a simplified partial perspective diagram illustrating one embodiment of a composite multi-layer material.
Figure 3:
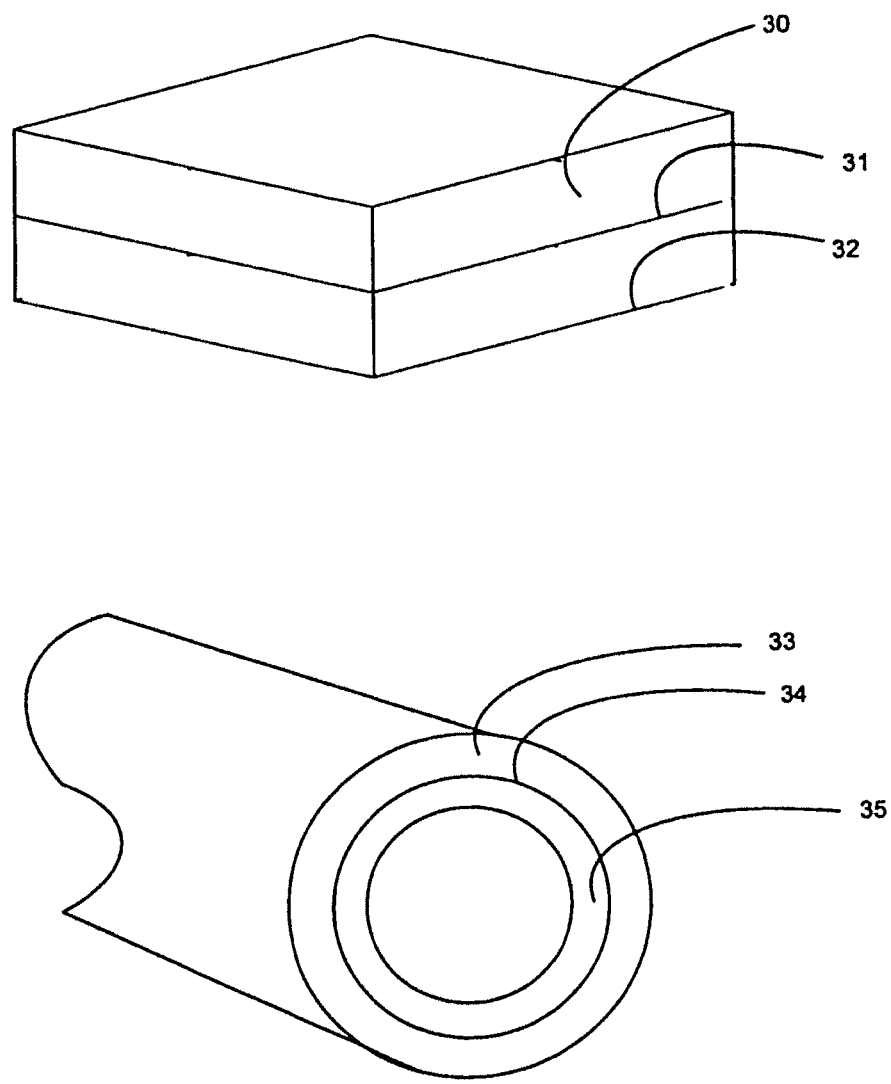
FIG. 3 is an illustration of the devices that can be formed from the composite multi-layer material.

Turning now to the drawing figures, it will be appreciated that FIG. 1 is a simplified partial perspective diagram, and FIG. 2 is an exploded partial perspective diagram, illustrating one embodiment of a composite multi-layer material. It will be appreciated that FIG. 3 is an illustration of embodiments of the devices that can be formed from the composite multi-layer material.

In accordance with some embodiments of a composite multi-layer material, at least a portion of a layer including d-PTFE 32 may be combined with or attached to at least a portion of a layer including an open structured material 30 to create a composite multi-layer material with an attachment region 31 between the layers. The interface between the layers may include attachment of partial areas of the layers or the interface may include attachment encompassing the entire surface of the interfaced layers.

In accordance with some embodiments of a composite multi-layer material, the composite multi-layer material may be formed into a flat structure with a layer including an open structured material, a layer including d-PTFE and an interface between the layers that may include attachment of a portion of the layers or may include an attachment between the layers encompassing the entire surface of the interfaced layers. Various different devices comprising the flat structured composite multi-layer material can be used in the repair of soft tissue. In many embodiments, the soft tissue for repair is in the chest. In many embodiments, the soft tissue for repair is in the abdomen.

In accordance with some embodiments of a composite multi-layer material, the composite multi-layer material may be formed into a tube structure having a inner layer including d-PTFE 35, an outer layer including an open structured material 33 and an interface 34 between the layers that may include attachment of a portion of the layers or may include an attachment encompassing the entire surface of the interfaced layers. Various different devices comprising the tube structured composite multi-layer material can be used in the repair of vascular tissue. Various different devices comprising the tube structured composite multi-layer material can be used as grafts for vascular tissue. In many embodiments, the vascular tissue for repair or grafting is in the chest. In certain embodiments, the vascular tissue for repair or grafting includes the vasculature including or surrounding the aorta. In certain embodiments, the vascular tissue for repair or grafting includes the coronary vasculature. In other embodiments, the vascular tissue for repair is in the abdomen. In other embodiments, the vascular tissue for repair is in the head and neck. In other embodiments, the vascular tissue for repair is in the arms and legs. In other embodiments, the vascular tissue for repair is in the groin area.

It will be appreciated that such attachment of the layers creating an interface may be accomplished by stitching layers of material, exertion of hydraulic or other pressure, application of a biocompatible adhesive or heat, or some combination of the foregoing. One or more combinations may be used in the attachment process. A composite multi-layer material constructed and operative in accordance with the present disclosure may have utility in applications related to the reconstruction of soft tissue defects of the chest and abdomen.

Because d-PTFE has no substantially defined internodal distance and can be manufactured with significantly less porosity than e-PTFE, and because it has exhibited no tendency to form adhesions when used in oral and maxillofacial surgical applications, the use of a d-PTFE, unexpanded material on the visceral side of a soft tissue composite multi-layer material may minimize or even eliminate the incidence of abdominal adhesions and post-operative complications as compared to existing devices. In addition, it will be appreciated that the material may be used to create a tube for use as a vascular prosthetic capable of permitting blood flow through the interior of the graft while providing an open structured material on the exterior to permit tissue colonization.

The terms "sintered" and "sintering process" are terms well known in the art and are used herein consistent with their understanding by those skilled in the art. Upon sintering, PTFE may be expanded to obtain a desired internodal distance and porosity. The term unsintered is used herein to describe PTFE that has not been subjected to the sintering process. Unsintered PTFE is substantially unexpanded and contains no substantially defined internodal distance, which substantially reduces its porosity relative to e-PTFE. The limited porosity of the unsintered, substantially unexpanded d-PTFE substantially reduces tissue adhesions to the d-PTFE or migration of tissue or cells into the d-PTFE. However, despite its limited porosity, unsintered and unexpanded d-PTFE allows for the passage of ions and other small molecules necessary for cellular nourishment and waste transport.

A composite multi-layer material constructed and operative in accordance with the present disclosure may have substantial, uniform strength in all directions, and may have at least one smooth side (e.g., comprising the d-PTFE layer to be exposed on the visceral side of the material during use). The composite multi-layer material may be constructed using d-PTFE having a hydrophobic, hydrophilic, textured or non-texture surface, combined with, or attached to, one or more open structured materials including unexpanded PTFE non-woven flatsheet; unexpanded PTFE woven materials; unexpanded PTFE mesh; expanded PTFE non-woven flatsheet; expanded PTFE woven materials, expanded PTFE mesh; polypropylene mesh; polypropylene woven materials and non-woven materials; resorbable polymer non-woven; resorbable polymer woven materials; resorbable polymer mesh; non-resorbable polymer non-woven materials; non-resorbable woven materials; non-resorbable mesh, or some combination of the foregoing. As noted briefly above, various techniques such as stitching, application of pressure, heat, adhesives, and the like, may be employed to effectuate the attachment of materials to form an interface between them. Such techniques may be application specific, and may vary in accordance with the type of materials to be attached, desired rigidity of the composite multi-layer material, and other factors. In operation, the composite multi-layer material may be sutured into place due to the nature of the material; additionally or alternatively, adhesives, staples, or other cooperating structural elements may be employed to place and to retain composite multi-layer material.

As noted above, conventional devices and techniques are generally deficient to the extent that they fail to contemplate use of high density or unexpanded PTFE in a composite multi-layer material for soft tissue repair. While laminated e-PTFE materials have been employed for soft tissue repair, the e-PTFE material is generally characterized by substantial porosity and defined internodal distances. In this context, internodal distance is a measurement used to describe the distance between the nodes and fibrils, a characteristic unique to e-PTFE only, and fundamentally describes the porosity or physical characteristics of the pores within the material. In contrast, the structure of the d-PTFE material set forth herein has no measurable, repeatable internodal distance as is commonly present with materials manufactured from e-PTFE.

Specifically, the d-PTFE material which may be implemented as the base material is a high density PTFE with a density in a range of about 1.2 grams/cc to about 2.3 grams/cc; for some applications, the density of d-PTFE may be in a range of about 1.45 grams/cc to about 1.55 grams/cc. As set forth above, the d-PTFE material may be unsintered and unexpanded having a nominal pore channel size of less than about 5 micrometers. In some embodiments, the unsintered, unexpanded d-PTFE may have a nominal pore channel size of less than 2 micrometers. In some embodiments, the unsintered, unexpanded d-PTFE may have a nominal pore channel size of less than 0.5 micrometers. In some embodiments, the unsintered, unexpanded d-PTFE may have a nominal pore channel size of less than 0.2 micrometers. This small pore channel size may allow a composite multi-layer material employing d-PTFE to exhibit superior functional characteristics, resulting clinically in reduced host response (inflammation), soft tissue in-growth, and resultant adhesions.

Several features and aspects of the present invention have been illustrated and described in detail with reference to particular embodiments by way of example only, and not by way of limitation. Those of skill in the art will appreciate that alternative implementations and various modifications to the disclosed embodiments are within the scope and contemplation of the present disclosure.

What is claimed is:

1. A method of treating a patient in need of tissue repair, comprising contacting the tissue in need of repair with a composite multi-layer material comprising:
    a first layer formed from unsintered substantially unexpanded polytetrafluoroethylene polymer and having a density in a range of about 1.2 gm/cc to about 2.3 gm/cc and having a plurality of pores having a nominal channel size of less than 5 micrometers; and
    a second layer formed from an open structured material, wherein surfaces of the first and second layers are attached at a common interface, wherein the first and second layers are attached by stitching at least a portion of said first layer to at least a portion of said second layer.

2. The method of claim 1, wherein the nominal channel size is less than 2 micrometers.

3. The method of claim 1, wherein the nominal channel size is less than 0.5 micrometers.

4. The method of claim 1, wherein the nominal channel size is less than 0.2 micrometers.

5. The method of claim 1, wherein the first layer has a hydrophobic surface.

6. The method of claim 1, wherein the first layer has a hydrophilic surface.

7. The method of claim 1, wherein the open structured material includes unexpanded PTFE.

8. The method of claim 7, wherein the open structured material forms a non-woven flatsheet.

9. The method of claim 7, wherein the open structured material forms a woven flatsheet.

10. The method of claim 7, wherein the open structured material forms a mesh.

11. The method of claim 1, wherein the open structured material includes polypropylene.

12. The method of claim 11, wherein the open structured material forms a non-woven flatsheet.

13. The method of claim 11, wherein the open structured material forms a woven flatsheet.

14. The method of claim 11, wherein the open structured material forms a mesh.

15. The method of claim 11, wherein the open structured material includes a resorbable polymer.

16. The method of claim 15, wherein the open structured material forms a non-woven flatsheet.

17. The method of claim 15, wherein the open structured material forms a woven flatsheet.

18. The method of claim 15, wherein the open structured material forms a mesh.

19. The method of claim 1, wherein the open structured material comprises a non-resorbable polymer.

20. The method of claim 19, wherein the open structured material forms a non-woven flatsheet.

21. The method of claim 19, wherein the open structured material forms a woven flatsheet.

22. The method of claim 19, wherein the open structured material forms a mesh.

23. The method of claim 1, wherein the first and second layers are attached using a biocompatible adhesive.

24. The method of claim 1, wherein the first and second layers are attached using heat.

25. The method of claim 1, wherein said composite multi-layer material forms a tube structure wherein said first layer forms the tube's interior surface and said second layer forms the tube's exterior surface.

26. The method of claim 1, wherein the polytetrafluoroethylene polymer of the first layer has a density in the range of 1.45 gm/cc to 1.55 gm/cc.

27. The method of claim 1, wherein the tissue in need of repair comprises a hernia.

* * * * *